(12) United States Patent
Hoffman

(10) Patent No.: US 7,195,014 B2
(45) Date of Patent: Mar. 27, 2007

(54) PORTABLE CONTINUOUS POSITIVE AIRWAY PRESSURE SYSTEM

(75) Inventor: Leslie Hoffman, Tarzana, CA (US)

(73) Assignee: Hoffman Laboratories, LLC, Chatsworth, CA (US)

( * ) Notice: Subject to any disclaimer, the term of this patent is extended or adjusted under 35 U.S.C. 154(b) by 0 days.

(21) Appl. No.: 11/128,552

(22) Filed: May 13, 2005

(65) Prior Publication Data

US 2006/0213516 A1 Sep. 28, 2006

Related U.S. Application Data

(60) Provisional application No. 60/664,108, filed on Mar. 22, 2005.

(51) Int. Cl.
*A62B 7/00* (2006.01)
*A62B 17/00* (2006.01)
(52) U.S. Cl. .............................. 128/204.18; 128/202.11
(58) Field of Classification Search ........... 128/201.29, 128/202.11, 202.18, 202.19, 204.18, 205.22, 128/205.18, 201.27, 204.22, 204.23
See application file for complete search history.

(56) References Cited

U.S. PATENT DOCUMENTS 4,019,508 A * 4/1977 Der Estephanian et al. ..... 128/142.7
H1360 H * 10/1994 Grove et al. ............ 128/201.25

OTHER PUBLICATIONS

Halberstadt, Jerry, Battery Operation of CPAP Devices for Sleep Apnea Treatment, Part 2: A battery backup system for use with CPAP treatment, New Technology Publishing, Inc., http://www.newtechpub.com/sleep/magazines/psnews/power02.html.

* cited by examiner

*Primary Examiner*—Henry Bennett
*Assistant Examiner*—Amadeus Lopez
(74) *Attorney, Agent, or Firm*—Beck & Tysver P.L.L.C.

(57) ABSTRACT

A portable, wearable vest supports an air supply tube to a patient mask or interface in a continuous positive air pressure system. In one embodiment, the vest contains and supports motor and battery components. In another embodiment, the vest couples a remote CPAP unit to a patient interface.

2 Claims, 6 Drawing Sheets

PORTABLE CONTINUOUS POSITIVE AIRWAY PRESSURE SYSTEM

CROSS REFERENCE TO RELATED APPLICATION

This application claims the benefit of U.S. Provisional Application No. 60/664,108, filed Mar. 22, 2005, which is incorporated herein by reference.

BACKGROUND OF THE INVENTION

Continuous positive airway pressure (CPAP) therapy is widely known. This therapy is predominately used to treat obstructive sleep apnea (OSA), as well as other disorders. CPAP therapy is used to deliver pressurized air, to a patient's airway. In general, conventional CPAP systems include a bedside "generator" that operates off either wall current or a large external battery. This generator is a blower or pump that creates a supply of pressurized air. A physician would typically prescribe a maximum CPAP in the range of 5–15 cm of water to treat the disorder. For patient comfort, the generator device may "ramp up" to the prescribed pressure over a period of several minutes.

The bedside generator is connected to the patient via a long flexible hose that transports the pressurized air from the generator to an interface worn by the patient. The term of art in this industry for the mask-like portion of the system is "interface" and the term is generic for oral, oral-nasal, or nasal designs. There are a wide variety of interfaces that are used and preferred by patients. It is important that the interface fit the patient securely to deliver pressurized air without substantial leakage.

SUMMARY OF THE INVENTION

The present invention is a portable CPAP unit that integrates a blower unit into a vest worn by the patient. In general the vest is relatively thick and made of foam covered with a cloth material. In one embodiment the vest provides space to house both the air handling system, power supply and control electronics in a balanced arrangement around the neck.

The vest includes a collar portion that is worn around the neck. The collar portion connects with first and second extended panel portions carried over the shoulder onto the chest of the user. The vest is shaped such that its profile adjacent the patient's neck fits within the contours of the patient's neck and is sized so that it does not protrude beyond planes defined by the patient's body.

In one preferred embodiment the vest contains a blower unit. The blower unit includes a clamshell housing defining a complex air path for a motor/impeller unit that is also contained within the clamshell housing. The motor/impeller unit and its associated diffuser housing are mechanically isolated from the clamshell housing, and together they form the blower unit.

A motor control unit and battery pack are placed within the vest to create a self-contained portable wearable CPAP device for treating obstructive sleep apnea (OSA) and other disorders.

In an alternate embodiment the vest itself is coupled to the remote air pressure generator and it serves to transfer air from the generator to the interface. In this embodiment the vest serves to decouple the user and most importantly the nasal interface from the remote generator. It has been found that decoupling the mask improves acceptance of the therapy and in this embodiment the vest allows air to pass through the vest from the generator to the interface.

BRIEF DESCRIPTION OF THE DRAWINGS

Throughout several figures identical reference numerals refer to identical structure wherein.

DETAILED DESCRIPTION OF THE PREFERRED EMBODIMENT

Figure 1:
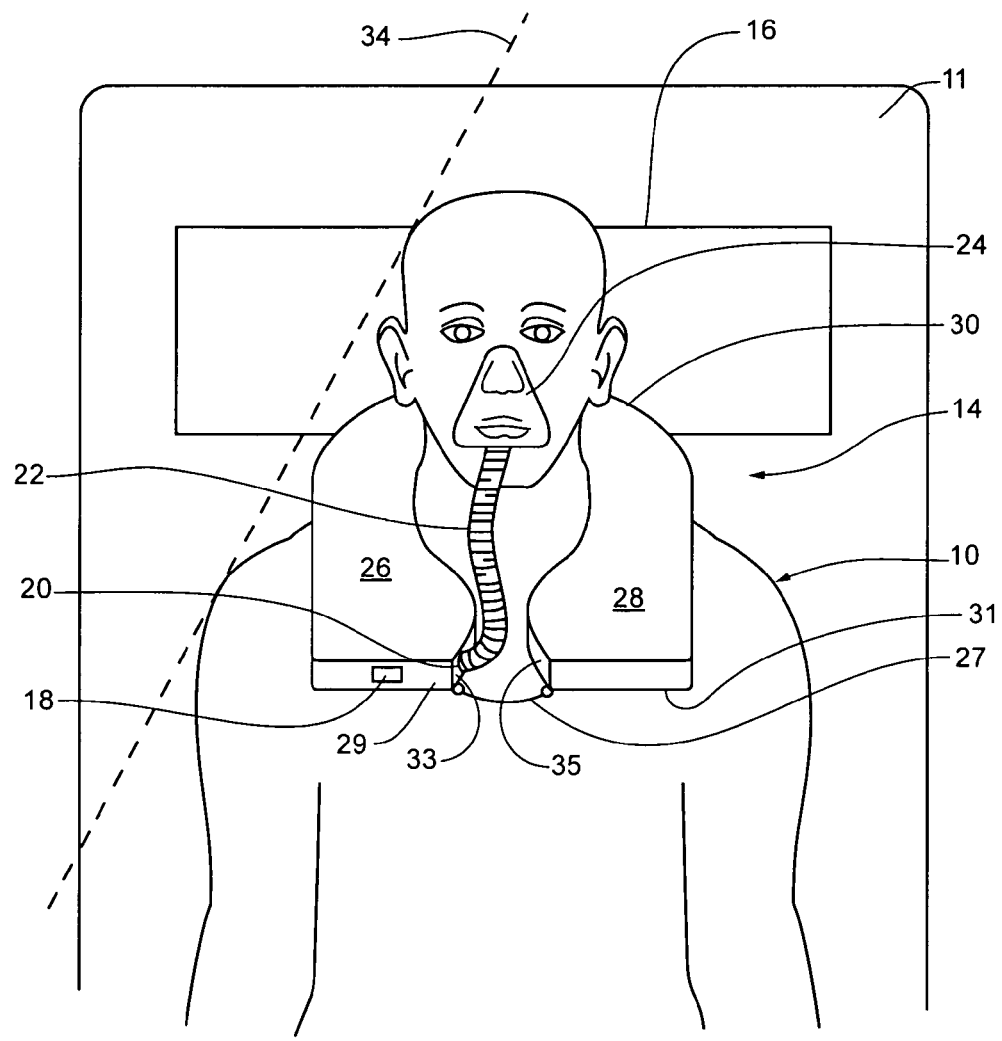
FIG. 1 is a schematic top view of a patient, lying down, wearing the wearable CPAP unit.

FIG. 1 shows the general configuration of a portable self-contained wearable CPAP vest 14 being worn by a patient or user 10 who is depicted in a supine position on a bed 11 with a pillow 16 under his head.

Figure 2:
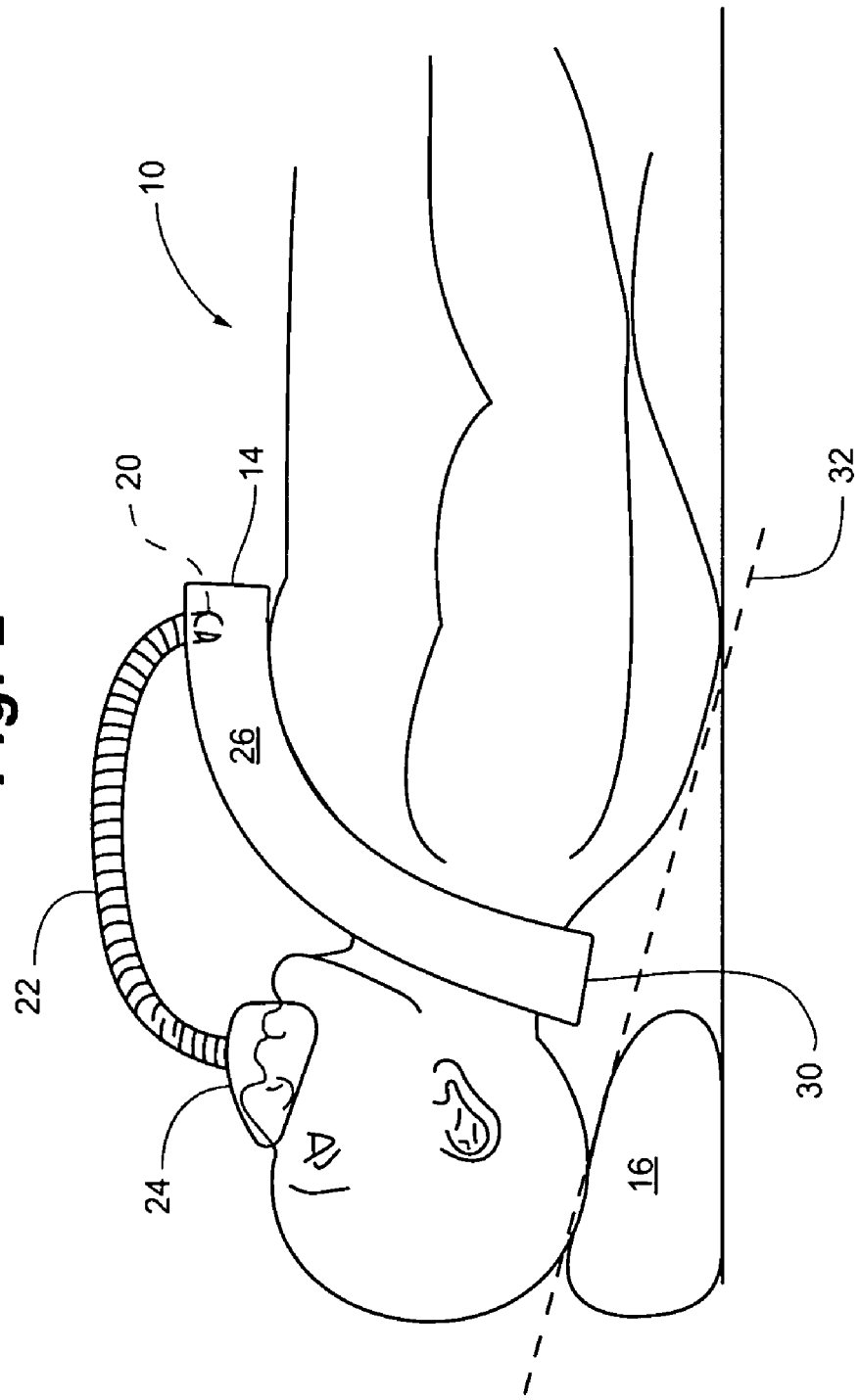
FIG. 2 is a schematic side view of a patient wearing the portable CPAP unit.

The vest 14 has a rounded neck portion or collar 30 positioned at the nape of the neck of the user. The collar 30 connects with and flares out onto a first panel 26 and a second panel 28 that lie over the chest of the user 10. Each panel 26, 28 has a lower edge 29, 31, respectively, and an inner edge 33, 35, respectively. The optimal size and shape of the collar 30 and the panels 26 and 28 will depend upon the stature of the user 10. In general, it is desirable that the cross-section of the collar 30 proximate the neck of the user be of reduced cross-section or diameter, and have a contoured shape such that it fits within the nape of the neck and does not act as a "pillow" or interfere with the patient's actual pillow 16 when the patient 10 reclines. This relationship is depicted in FIG. 2 which shows a supine patient 10 and an associated plane 32 defined by and extending from the back of the head to the shoulder blades. It is preferred to have the collar 30 not completely fill the nape of the neck so that the collar 30 does not touch or extend beyond the plane 32 toward the bed 11.

Returning to FIG. 1, it is also preferred to have the exterior edges of the panel portions 26 and 28 lie within the shoulder-width of the patient and within the head-to-shoulder plane identified by reference numeral 34 in FIG. 1. It has been found that when these several conditions are met the patient 10 may rest on his side and roll over in his sleep with the head and shoulders in a natural posture. When appropriately sized, the collar 30 and panels 26, 28 do not interfere with the comfort of the patient. These geometric and dimensional attributes define the shape of a vest 14 that may be worn unobtrusively during sleep. It has been found that these design attributes associated with these cross-sectional areas and bulk of the panels are designed not to interfere with patient comfort.

Also shown in FIG. 1, the connection hose 22 couples the vest 14 to a user interface or mask 24. The mask 24 serves as an air delivery device and other interfaces may be readily substituted within the context of the invention. The proximal end of the hose 22 couples to one panel portion 26 of the vest 14 at an outlet 20. In operation, air entering the vest via inlet 18 is pressurized within the vest 14 and transferred to the hose 22 and thence to the mask 24 or other interface structure.

The distal ends of the panels 26 and 28 may be connected together by a clasp 27 or other device to keep the vest oriented on the patient. In a similar fashion the panels may be fixed to the clothing of the user 10 by structures (not shown) to maintain orientation of the panels 26, 28 with respect to the chest of the user.

Figure 3:
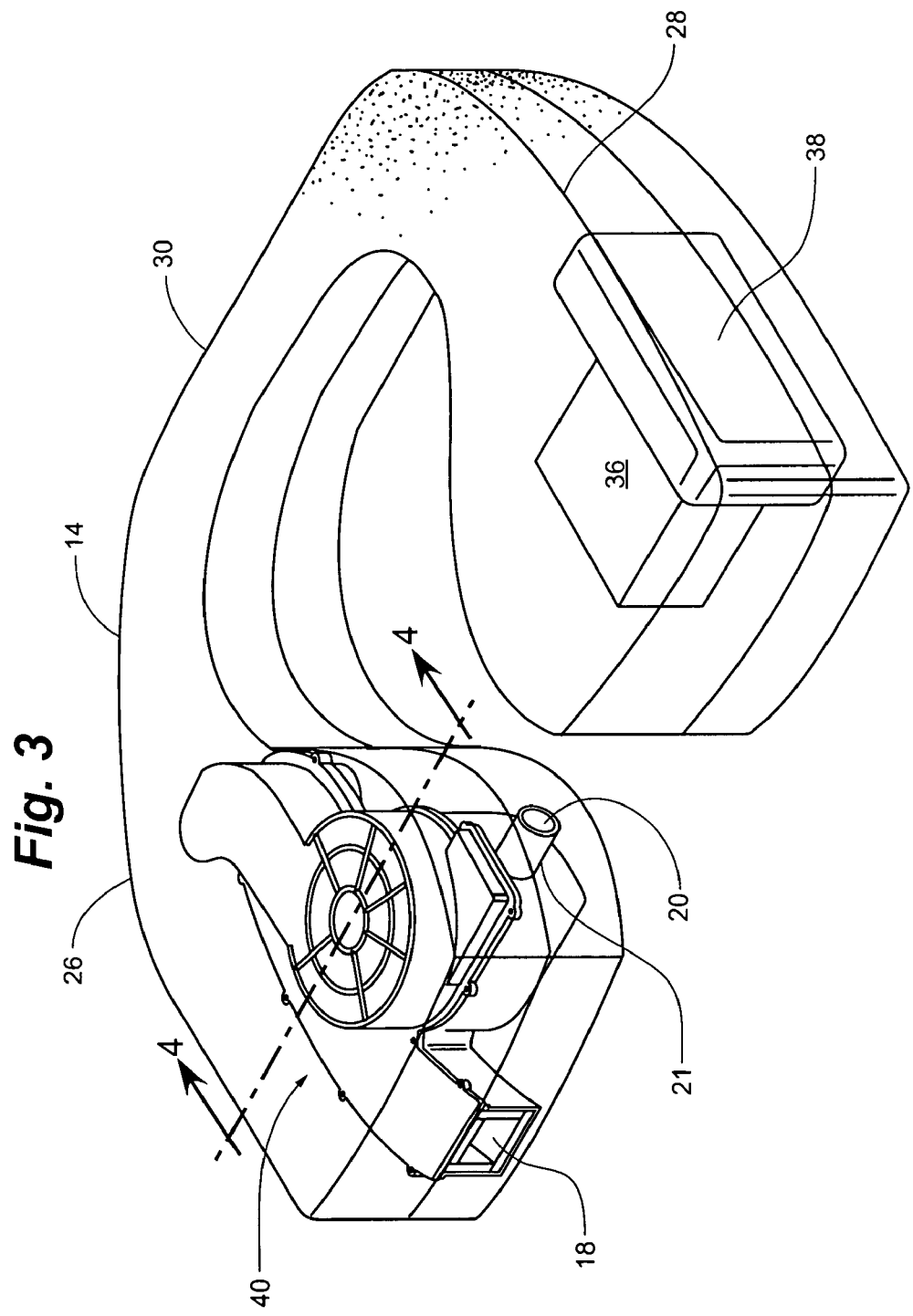
FIG. 3 is an isometric view showing the orientation, relationship and position of various elements of the wearable CPAP unit.

FIG. 3 shows a blower unit housing 40 in panel 26 of the vest 14. This blower unit housing 40 contains within it, a motor/impeller and associated diffuser scroll unit 42. Many mechanical features and structures and relationships further described, have been found to be effective in suppressing noise generated by the pressurization of air within the vest 14. These features are described in connection with FIG. 4. In general the blower unit housing 40 and motor/impeller unit have together several attributes that will, in combination, produce a very quiet blower that is believed to be an important characteristic for acceptance of the vest by the user. It is advantageous for the motor impeller unit to use very low power to allow portable battery operation and to prevent excessive heat build up in the device or in air exiting the device.

The second panel 28 of the vest 14 contains a battery pack 36 coupled to an electronic motor control unit 38. The battery pack 36 being compact in nature and has sufficient capacity to operate the vest 14 for periods of time approximating ten hours or so. Buttons (not shown) on the control unit 38 are exteriorized for use by the patient 10. The control unit 38 carries motor control functions (e.g. an on/off switch) and a charging receptacle or jack to permit the patient 10 to recharge the battery pack 36.

The partitioning of the battery pack 36, control unit 38 and blower unit housing 40 is intended to equalize the weight of the side panels 26 and 28 to make them roughly equivalent, which helps maintain the vest 14 in position on the wearer or user 10. To achieve this result, it is permissible to reorganize the distribution of weight throughout the vest and it is anticipated that the battery pack may be split or placed elsewhere in the vest 10. Electrical connections, not shown to simplify the figure, are buried within the foam of the vest 10 and connect the control unit 38 with the battery pack 36 and the motor within the blower unit housing 40.

It is preferred, but not essential, that the motor blower unit 40 exhaust its output to a location near the center line of the patient 10. A short hose 22 couples the outlet 20 to a user interface or distribution device, such as a mask 24 (shown in FIG. 1) or nasal cannula (not shown) to provide CPAP flow to the patient's airways. A short light hose 22 produces less pull on the mask 24 or interface worn by the patient promoting less movement of the mask on the patient face with subsequently a better seal. Also, not being connected to a bed-side CPAP unit provides freedom of movement for the patient.

It is also preferred, but not essential, to have the air inlet 18 for the blower unit housing 40 near the bottom of one side, or adjacent one panel, of the vest 14 as seen with reference to inlet 18 on FIG. 1 and FIG. 2. This location directs noise away from patient and bed partner and is generally unobstructed during sleep for most patients. Other alternative locations are contemplated including connections on the upper surface of the collar or panel away from the patient.

It is the applicants' view that acceptance of a portable CPAP unit depends in large measure upon suppressing to the extent possible noise created by the motor blower unit. The existence of a loud motor next to the patient would be disconcerting and uncomfortable, and thereby may reduce usage, so every effort is made and a substantial effort is directed to designing the motor to suppress sound described in connection with FIG. 4.

Figure 4:
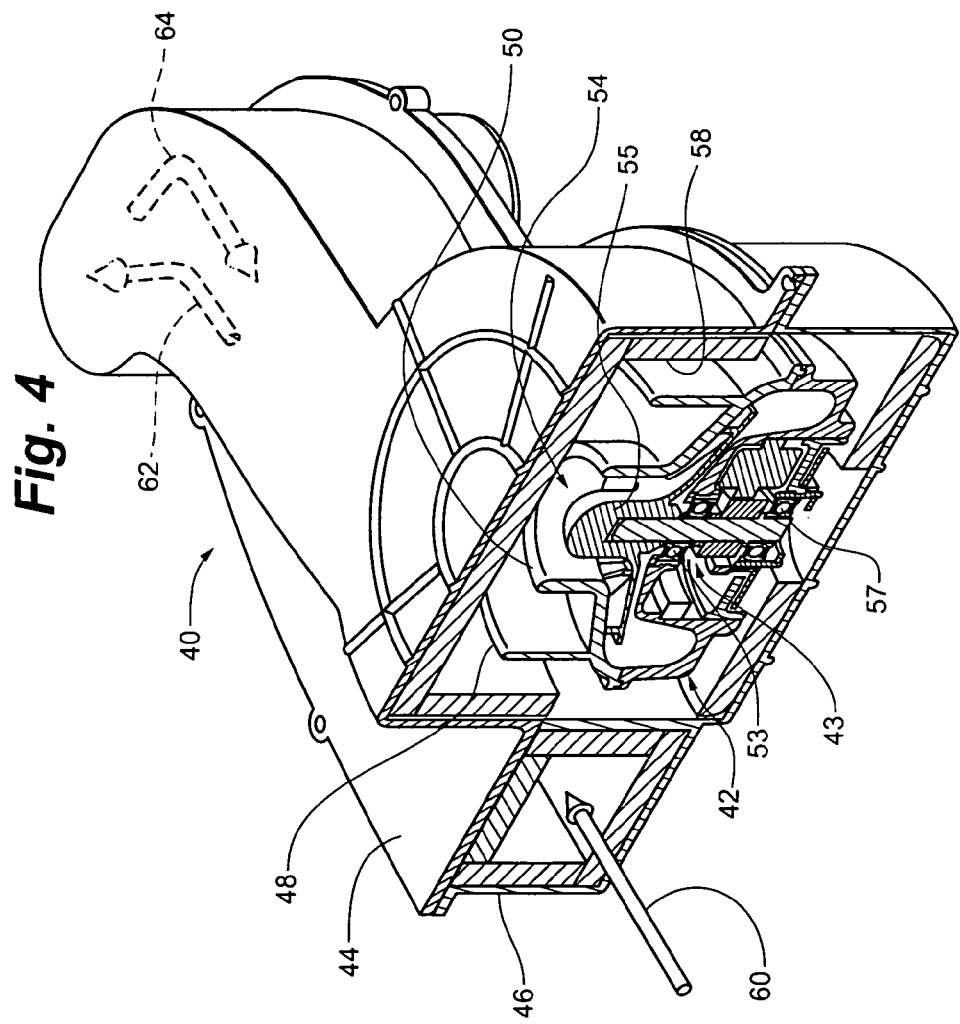
FIG. 4 is an isometric view of the impeller diffuser inlet and outlet portion of the device.

In FIG. 4, the blower unit housing 40 is shown with a cross-section taken at line 4—4 in FIG. 3. This figure depicts the motor/impeller and associated scroll housing 42 contained within the blower housing 40. The clamshell housing 40 defines a labyrinthine air path between an inlet 18 to the motor/impeller unit inlet annulus 54. The motor/impeller and scroll unit 42 accelerate the airflow and increase the kinetic energy in the airflow. The diffuser scroll is formed integrally with the motor and it serves to convert the kinetic energy to a static pressure delivered to the outlet 20 that is also the end of the "scroll" passage shown as the short tube 21.

DC brushless motor elements are adjacent to the impeller wheel 55. The impeller wheel 55 is supported cantilever fashion on an axle by two bearings 53 and 57, each of which is below the impeller 55. The motor elements, impeller 55, and diffuser scroll 42 form an independent mechanical unit that is isolated from the blower housing 40. It may be suspended by or mounted on a foam pad or a set of rubber standoffs (not shown). Thus, the motor/impeller elements lie within a "cocoon" like chamber 58 and are mechanically isolated from the remainder of the blower unit 40.

Returning to the blower housing 40 the preferred construction is a clamshell with a top 44 or lid fitting on top of a lower 46 clamshell portion. The housing is lined with a foam and it has a complex passage diverting air flowing along path 60 through two ninety degree turns depicted in the figure by flow arrows 62 and 64 to turn the airflow through a tortuous path to the inlet annulus 54 of the impeller 55. As the airflow approaches the annulus 54 it passes over a first annular baffle 48 and then a second annular baffle 50. These baffles help suppress the radiation or conduction of noise emanating from the motor/impeller.

In the preferred embodiment of FIG. 1, the vest 14, as described above, houses and supports operational components such as the blower unit housing 40 with motor impeller and scroll unit 42, the battery pack 36 and the control unit 38. In addition, the vest 14 supports the hose 22 that carries air from the operational components to the user interface 24. One of the advantages achieved by this arrangement over the conventional bedside CPAP machine is that forces that tend to pull a mask away from a patient's nose and mouth are significantly reduced. Thus, the "head gear" required to hold the interface to the patient's face need not be elaborate. The embodiment of FIG. 1 lacks the conventional straps used to secure the interface to the face. The vest is very stable in position on the patient and most patient motion does not result in significant forces applied to the mask or interface. If the compliant tube 22 is biased toward the face, then a force is generated to retain the interface on the face.

Figure 5:
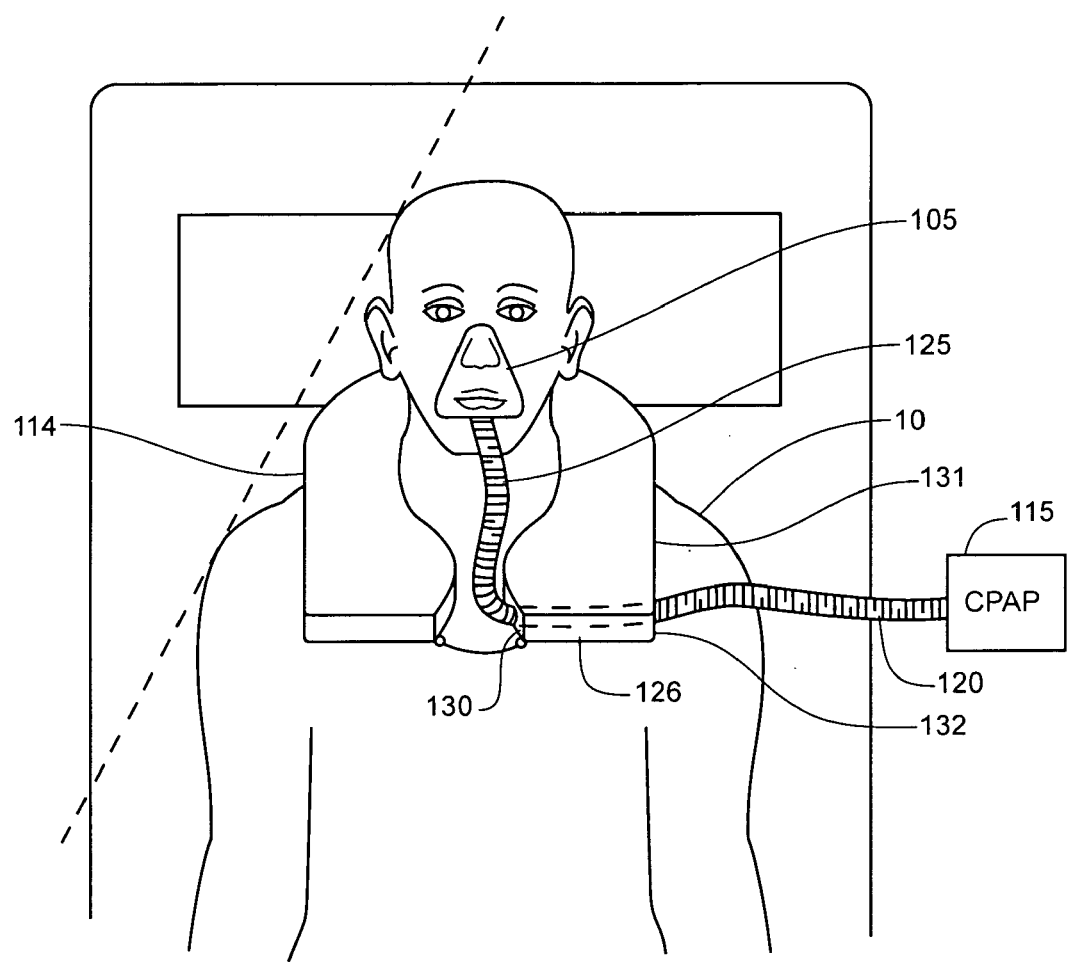
FIG. 5 is a schematic top view of an alternate embodiment.

FIG. 5 depicts an alternative embodiment where a user interface 105 connects via a vest 114 to a traditional bedside CPAP unit 115. The vest 114 supports a hose section 120 between the vest 114 and the CPAP unit 115. In addition, the vest 114 supports a hose section 125 between the vest 114 and the user interface 105. Hose sections 120 and 125 are in fluid communication, and may be continuous or may be in discrete sections, to allow air from the CPAP unit to pass to the user interface 105. The vest may include a conduit 126 passing from the inside edge 130 of one panel 131 to the outside edge 132 of the panel 131, with hose section 125 connected to the inside edge and hose section 120 connected to the outside edge.

The vest 114 bears and disperses to the patient's torso the mechanical forces transmitted by the hose section 120, so that those forces are not transmitted to the hose section 125. In this manner, the user interface 105 is de-coupled from these forces and therefore the interface is held in place without significant head gear. The FIG. 5 embodiment provides no straps to hold the mask in place. The vest 114 may include operational components, as described above with respect to the FIG. 1 embodiment, and allow the user to selectively couple the hose section 125 to the outlet of the in-vest blower or to the outlet of a conventional bedside CPAP unit, as desired.

Figure 6:
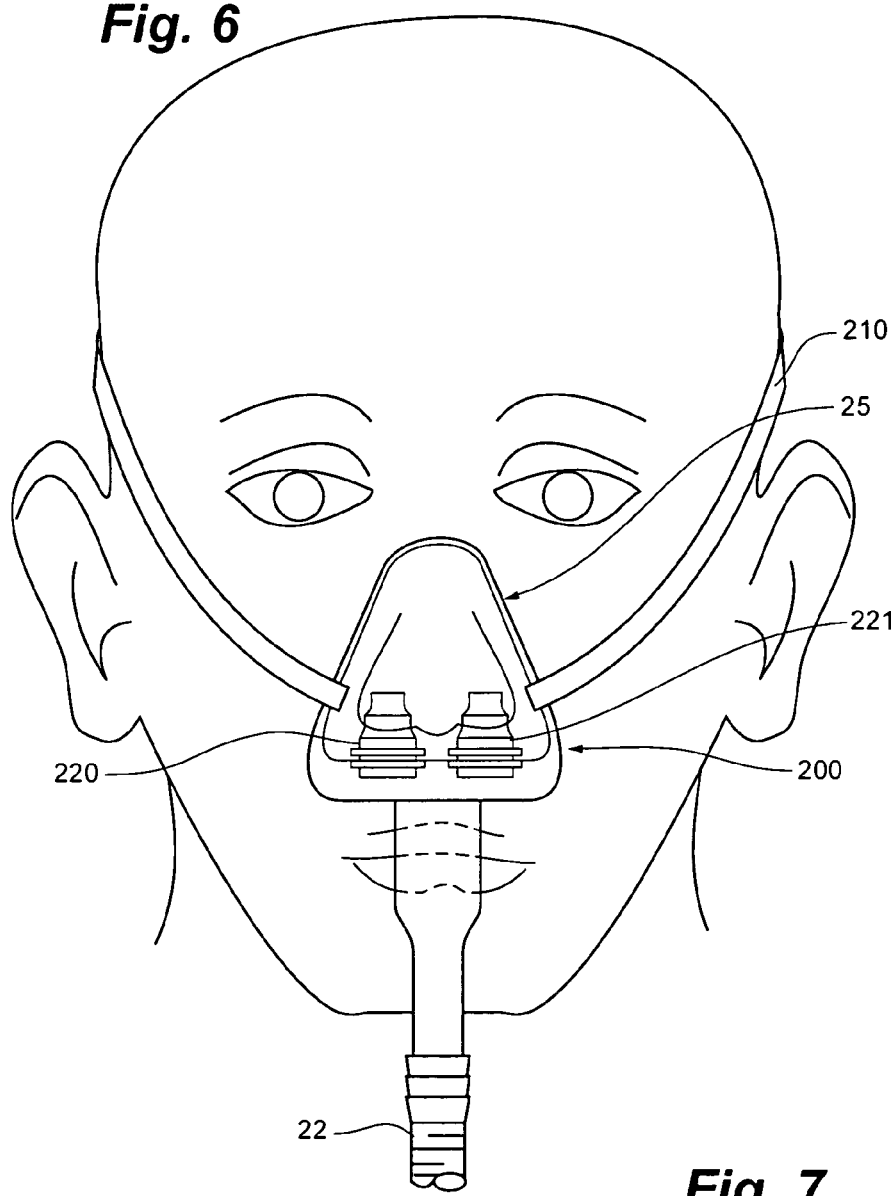
FIG. 6 is a view of an interface particularly suited for use in the system.
Figure 7:
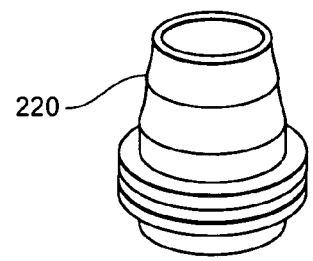
FIG. 7 is an enlarged perspective view of one of the cannulas of the interface of FIG. 6.

FIG. 6 shows a nasal mask or interface 200 that uses only very "light" retention straps 210 to keep the interface 200 on the face of the user. The mask 200 includes two nasal cannulas 220, 221 which, in use, are inserted into the patient's nostrils. These cannulas or portals 220, 221 are designed to experience minimal lateral movement and are stabilized by the mask 200 fitted over the patient's nose. The mask 200 is sized to cover the patient's nose, but not the mouth. FIG. 7 illustrates one of the cannulas 220.

What is claimed:

1. A portable wearable continuous positive air-pressure system of the type used for the treatment of obstructive sleep apnea and other disorders by a patient comprising:

a vest having a collar adapted for location in the nape of the neck of said patient;

said collar sized to lie within the nape of the neck and to not protrude through a plane defined by the back of the patient's head and the patient's shoulder blades;

a first panel coupled to said collar lying on the chest of the patient;

a second panel coupled to said collar and lying on the chest of the patient;

said first and second panels sized to lie on the chest of the patient and not protrude past a plane extending from the patient's head to the patient's shoulder;

a blower unit housing positioned within said first panel proximate its lower edge having an air inlet at the lower edge and having an outlet on an inner edge to provide output air under pressure;

brushless DC motor elements coupled to an impeller wheel located within said blower unit housing supplying air to an outlet from an inlet;

said brushless DC motor elements coupled to a motor control unit located in said second panel at a position close to the lower edge;

a battery pack coupled to the control unit, the control unit having motor control functions present on one said panel accessible by the patient; and a compliant hose biased to supply a force on an interface positioned on the face of the patient, said hose coupled to said outlet, whereby air is transferred from said vest to the patient under pressure.

2. A portable wearable continuous positive air-pressure system according to claim 1, wherein said hose is of a short length, spanning the distance from proximate the user's chest to the user's face.

* * * * *